United States Patent [19]

Bettinger

[11] Patent Number: 5,607,055
[45] Date of Patent: Mar. 4, 1997

[54] VACUUM PACKAGE FOR FLEXIBLE PRODUCTS

[75] Inventor: George E. Bettinger, Lake Jackson, Tex.

[73] Assignee: Mallinckrodt Medical, Inc., St. Louis, Mo.

[21] Appl. No.: 403,996

[22] Filed: Mar. 14, 1995

[51] Int. Cl.⁶ .......................... B65D 83/10; B65D 81/20
[52] U.S. Cl. ........................ 206/364; 206/524.8
[58] Field of Search ................ 206/524.8, 364, 206/363, 560, 561, 564, 565

[56] References Cited

U.S. PATENT DOCUMENTS

| | | | |
|---|---|---|---|
| 4,019,633 | 4/1977 | Roth | 206/364 |
| 5,082,112 | 1/1992 | Dunklee | 206/363 |
| 5,105,942 | 4/1992 | van Veen et al. | 206/364 |
| 5,165,540 | 11/1992 | Forney | 206/364 |
| 5,284,244 | 2/1994 | O'Toole et al. | 206/363 |

Primary Examiner—Bryon P. Gehman
Attorney, Agent, or Firm—Wendell Ray Guffey; Roy J. Klostermann; David A. Hey

[57] ABSTRACT

The present invention relates to packages for flexible products, especially medical products, wherein the package maintains the product in a desired configuration without kinking and allows for easy withdrawal of the product from the package. In a preferred embodiment, the present invention relates to a package for a medical catheter, the package having vacuum-formed ridges providing longitudinal stability to the package without interfering with the ability to easily remove the product from the package. The present invention further relates to methods of packaging flexible products using the packages according to the present invention.

1 Claim, 2 Drawing Sheets

VACUUM PACKAGE FOR FLEXIBLE PRODUCTS

BACKGROUND

The present invention relates to packages for flexible products, especially medical products, wherein the package maintains the product in a desired configuration without kinking and allows for easy withdrawal of the product from the package.

The present invention further relates to methods of packaging flexible products using the packages according to the present invention.

For ease of explanation, the present invention will be described with respect to a medical catheter, although it will be recognized that the present invention is equally applicable to other flexible products, both in the medical field and other fields. Currently, flexible products, such as medical catheters, are often packaged in a two piece assembly including a plastic or paper tray, and a preformed pouch. The tray may have formed therein depressions or other means in which the catheter is fixed to maintain a desired configuration. Once the catheter is fixed to the tray, this assembly is inserted into the pouch and the pouch is sealed. Alternatively, the catheter may be simply inserted into a pouch without any other support.

Tray and pouch packages result in two pieces of waste, which is becoming more and more undesirable from the aspect of waste disposal. Further, in known packages, the tray must be specialized to include features to hold the catheter in place. Simple pouch packages have the disadvantage of not providing sufficient stability to the catheter during shipping and handling.

Therefore, there remains a need in the art for improvements to packages for flexible products, such as medical catheters.

OBJECTS OF THE INVENTION

It is one object of the present invention to provide a package for a medical product, such as a catheter, which provides a high degree of longitudinal stability to avoid damage to the catheter during shipping and handling but which allows easy withdrawal of the catheter from the package without undue stress to the preformed curves or bends of the distal tip of the catheter.

It is a further object of the present invention to provide a method of packaging catheters using the packages according to the present invention.

SUMMARY OF THE INVENTION

These objects and others are accomplished according to the present invention by providing a specialized package which includes stiffening means for retaining a flexible product without kinking. The package according to the present invention further allows for easy removal of the product without straightening of any curve or bend which may be formed in the product.

DETAILED DESCRIPTION OF THE INVENTION

The present invention will be described with reference to packages for medical catheter products but it will be recognized that the present invention would be equally applicable to packages for other types of flexible products.

As noted above, catheters may be packaged using a preformed plastic or paper tray and a separate preformed pouch. The tray normally includes means, such as cutouts or depressions, to secure the catheter. To use the catheter, the pouch is opened and the tray is removed from the pouch. The device may then be lifted free of the securing means, which may cause undue strain or stress to the catheter. In addition, as noted above, this package creates a considerable amount of waste.

Catheters have also been packaged in simple pouches. While possibly having less waste then tray and pouch packages, simple pouches have the disadvantage of not providing enough longitudinal strength to the catheter during shipping and handling. This can lead to bending or folding of the package and ultimately to kinking of the catheter.

Packages comprising a tray, formed of plastic or paper, and a cover sheet, formed of plastic, have also been used to package medical devices. The tray may simply be a flat sheet of paper or plastic onto which the catheter is placed. The cover sheet is then sealed to the tray. These packages help to reduce the amount of waste associated with the package, because secondary means of support, such as a surrounding pouch is necessary, but the trays often fail to provide enough longitudinal strength to prevent bending or folding during shipping and handling.

To improve stability, trays have been formed with depressions or grooves into which the catheter is deposited. These depressions are designed to hold the product in a particular location on the tray. However, in practice, these trays have proven to be deficient for several reasons. In particular, during shipment or handling, the catheter often works free of the depression or groove and therefore loses the desired and intended support. Alternatively, the catheter may reside below the groove area, thereby causing flattening or lateral bending of the catheter. Also, if the catheter remains in the depression or groove, stretching of the preformed curves or bends of the catheter may occur as the catheter is withdrawn through the depressions of the tray. This is highly disadvantageous as such straightening or stretching can create weaknesses or change the shape of the catheter and may lead to kinking during use.

The packages according to the present invention overcome the disadvantages noted above, as will become apparent from the detailed description below.

Figure 1:
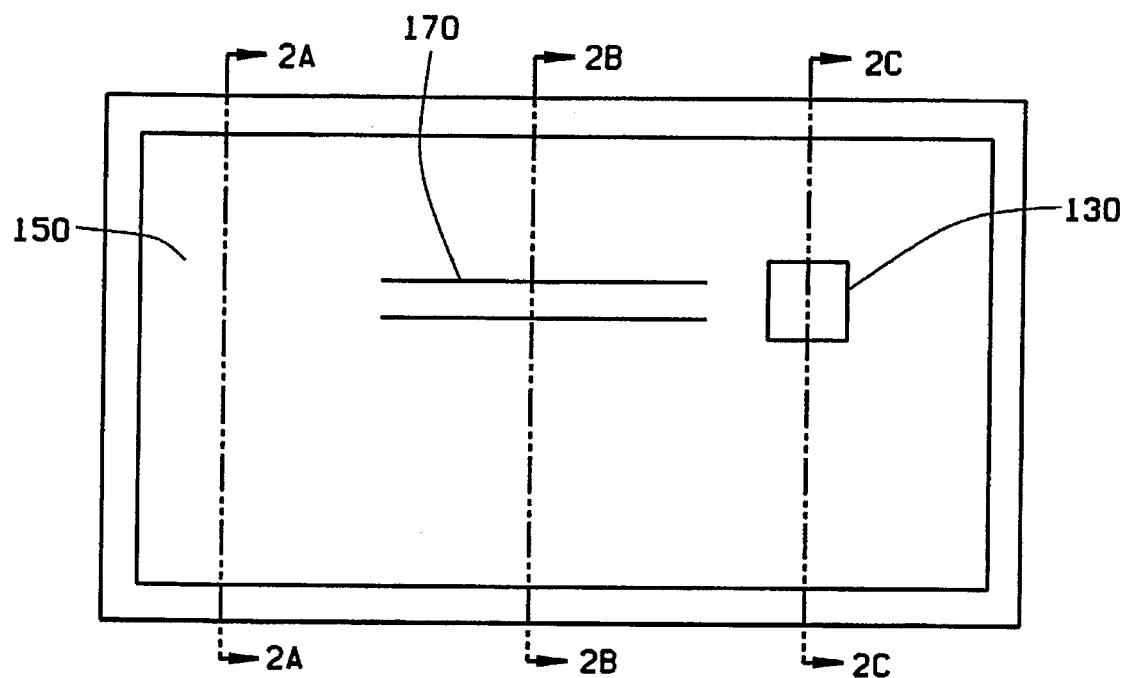
FIG. 1 is a top plan view of a portion of a package according to one embodiment of the present invention.

FIG. 1 is a top plan view of a portion of a package according to a preferred embodiment of the present invention. In particular, FIG. 1 shows a tray, generally designated by reference numeral 100, which includes a pair of ridges 170, formed along a portion of the length of the tray 100, and a hub retaining portion 130, formed near one end of the tray 100. As clearly shown in FIG. 1 the ridges 170, extend along only a portion of the length of the tray 100, and leave a relatively flat portion 150, of the tray 100, at the opposite end from the hub retaining portion 130. The hub retaining portion 130, comprises a rectangular area defined by four interconnected ridges set around its periphery.

The tray may be formed of paper or plastic using one or a combination of several well known techniques, such a pressing, molding, vacuum drawing or thermosetting. In the case of a plastic tray, the plastic may be softened using heat and then pressed, pushed or drawn into a mold to make the desired shape. In the case of a paper tray, similar techniques may be used or the paper may be stamped to create the desired shape. The tray may be formed from any material which is able to sustain a vacuum applied to the package as discussed below and which may be formed according to the methods noted above.

FIGS. 2A through 2F show more detail of the package shown in FIG. 1 and are particularly useful in describing the features and advantages of this package.

Figure 2A:
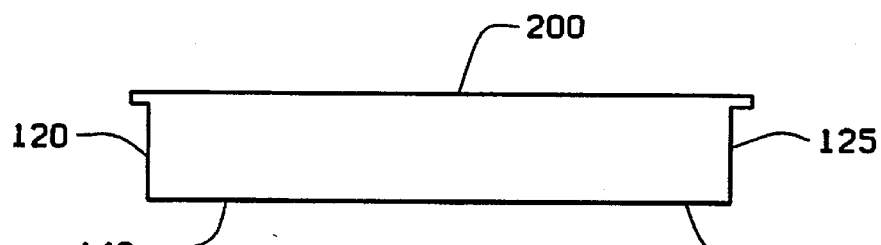
FIG. 2A is a cross sectional end view of a package according to the present invention taken along line A—A of FIG. 1 wherein the package is in an open condition.

FIG. 2A is a cross sectional end view taken along line A—A of FIG. 1 and shows the interaction of tray 100, and a cover sheet 200, prior to vacuum being applied. This figure also represents a portion of the package after the seal has been broken and the vacuum released upon opening of the package. As will be evident, the package according to the present invention becomes an open pouch upon release of the vacuum and thereby facilitates easy removal of the catheter from the package. The open pouch package creates no stress or strain to the distal end of the catheter or to preformed curves or bends therein as the catheter is being withdrawn from the package. The tray 100, is relatively stiff so as to maintain the tray configuration and includes side walls 120, 125, and a bottom 140. The side walls 120, 125, and bottom 140, interact upon vacuum being applied to the package to provide stabilizing edges, as will be discussed more fully below.

Figure 2B:
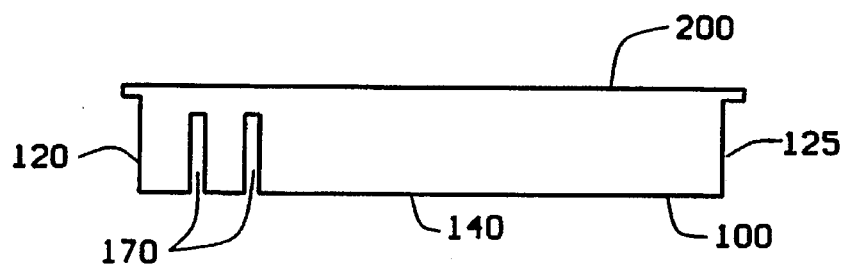
FIG. 2B is a cross sectional end view of a package according to the present invention taken along line B—B of FIG. 1 wherein the package is in an open condition.

FIG. 2B is a cross sectional end view taken along line B—B of FIG. 1 and again shows the interaction of tray 100, and the cover sheet 200, prior to vacuum being applied or after the seal has been broken and the vacuum released. The side walls 120, 125, also interact with the bottom 140, in this section to provide stabilizing edges, as will be discussed fully below. Also shown are the ridges 170, which form a trough within which a catheter is deposited. The ridges 170, securely hold the catheter when drawn together under vacuum and also help to avoid bending and damage to the product during shipping and handling.

Figure 2C:
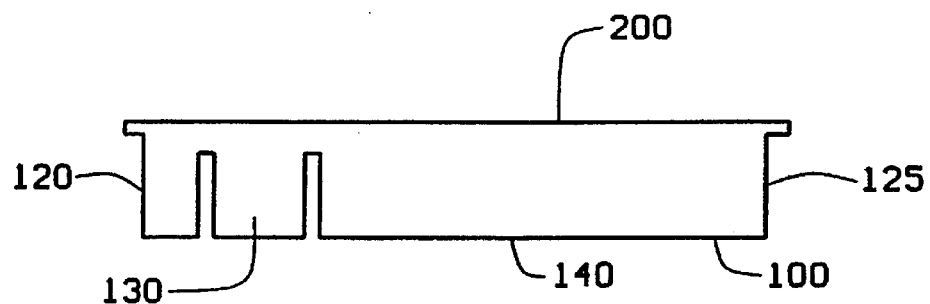
FIG. 2C is a cross sectional end view of a package according to the present invention taken along line C—C of FIG. 1 wherein the package is in an open condition.

FIG. 2C is a cross sectional end view taken along line C—C of FIG. 1 and also shows the interaction of tray 100, and the cover sheet 200, prior to vacuum being applied or after the vacuum has been released. FIG. 2C further shows side walls 120, 125, bottom 140, and hub retaining portion 130. It will be noted that the width of the hub retaining portion 130, is greater than the width between the ridges 170. This provides adequate space for retention of the hub of the catheter and facilitates removal of the catheter from the package. In this portion, the side walls 120, 125, and bottom 140, also interact to provide stabilizing edges.

Figure 2D:
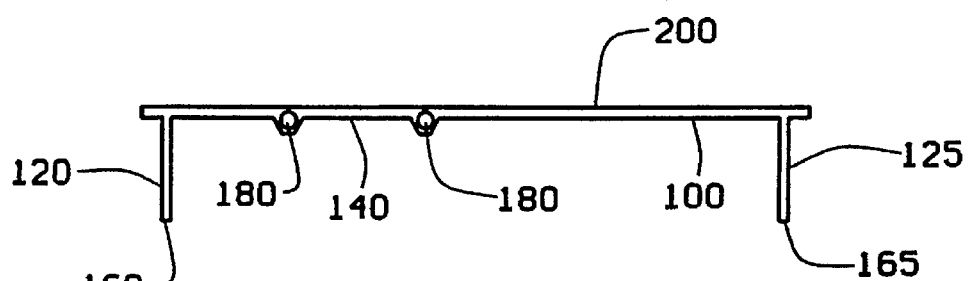
FIG. 2D is a cross sectional end view of a package according to the present invention taken along line A—A of FIG. 1 wherein the package is in a sealed and evacuated condition.

FIG. 2D is a cross sectional end view taken along line A—A of FIG. 1 and shows the interaction of tray 100, and the cover sheet 200, following application of vacuum to the package. In addition, portions of a distal tip of a catheter 180, are shown. When the vacuum is drawn within the package, the distal end of the catheter 180, is firmly held in place between the bottom 140, of tray 100, and cover sheet 200. In particular, any preformed curve or bend in the distal end of the catheter 180, is retained firmly in the desired configuration, without the need for additional pieces of packaging, such as cutouts or depressions. Because there are no shape retention means within this portion of the package, and because the package reverts to an open pouch upon opening and release of vacuum, as shown in FIG. 2A, removal of the catheter 180, from the package is facilitated and no straightening or stretching of the distal tip of the catheter 180, occurs. FIG. 2D also shows stabilizing edges 160, 165, which provide longitudinal strength to the package. The stabilizing edges 160, 165, are formed upon application of vacuum to the package. In particular, as vacuum is applied, the bottom 140, is pulled toward the cover 200. This creates an excess of material in the bottom 140, which naturally pushes out toward the side walls 120, 125. As vacuum increases, a portion of the bottom 140, aligns with each side wall 120, 125, to form the stabilizing edges 160, 165. The stabilizing edges 160, 165, add significantly to the longitudinal strength of the package and therefore help to prevent bending or folding of the package and ultimately the catheter during shipping and handling.

Figure 2E:
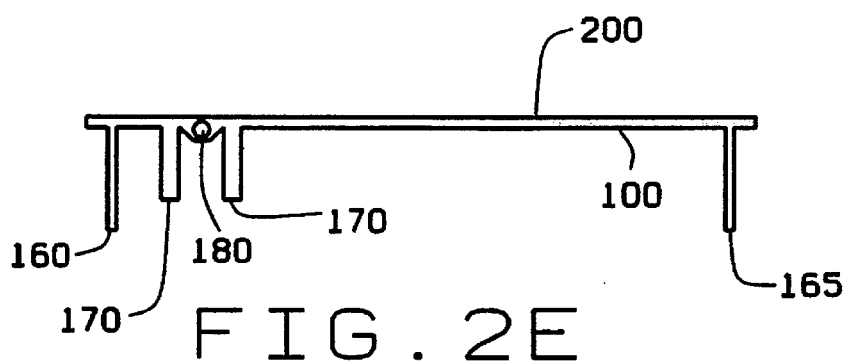
FIG. 2E is a cross sectional end view of a package according to the present invention taken along line B—B of FIG. 1 wherein the package is in a sealed and evacuated condition.

FIG. 2E is a cross sectional end view taken along line B—B of FIG. 1 and again shows the interaction of tray 100, and the cover sheet 200, following application of vacuum to the package. Also shown are the ridges 170 and the main trunk of the catheter 180. When the vacuum is drawn, the tray 100, pulls down between the ridges 170, and around the catheter 180, to firmly retain the catheter 180 between the ridges 170. In addition, the vacuum causes the ridges 170, to be urged toward one another to effectively encase the catheter 180, and prevent displacement during shipment and handling. FIG. 2E also shows the stabilizing edges 160, 165, which are formed upon application of vacuum to the package as described above.

Figure 2F:
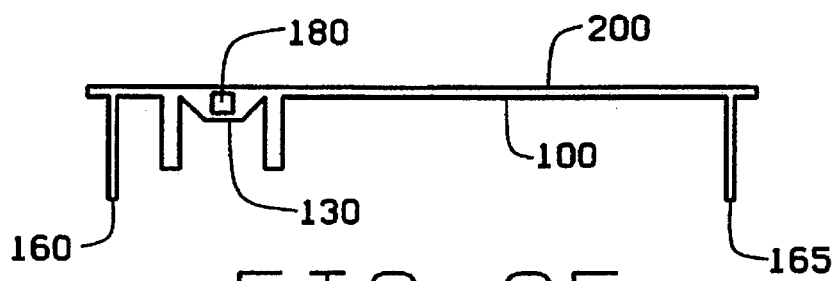
FIG. 2F is a cross sectional end view of a package according to the present invention taken along line C—C of FIG. 1 wherein the package is in a sealed and evacuated condition.

FIG. 2F is a cross sectional end view taken along line C—C of FIG. 1 and also shows the interaction of tray 100, and the cover sheet 200, following application of vacuum to the package. FIG. 2F further shows the hub retaining portion 130, and the hub of the catheter 180. When the vacuum is drawn, the tray 100, pulls down between the peripheral ridges of the hub retaining portion 130, and around the hub of the catheter 180. In this way the hub of the catheter 180, is kept securely in place until the package is opened by the user. Stabilizing edges 160, 165, are again shown and are formed in the same manner as described above.

Once the package is opened and the vacuum is released, the package reverts to its initial state as shown in FIGS. 2A, 2B and 2C. In particular, the tray 100, pulls away from the cover 200, and ridges 170, pull away from each other. In this state, the catheter may be easily grasped and removed from the package. The hub retaining portion 130, helps to keep the hub from shifting in the package once the package has been opened and thereby further facilitates grasping and removal of the catheter 180, from the package. The trough between the ridges 170, loosely holds the main body of the catheter 180, which may easily be lifted free. The preformed curves at the distal end of the catheter 180, are freed from the bottom 140, and cover 200, and therefore are not straightened or stretched upon removal from the package.

In use, a catheter 180, is deposited onto the tray 100, with the hub of the catheter 180, located within the hub retaining portion 130, the main trunk of the catheter 180, in between the ridges 170, and the preformed curved distal end of the catheter 180, in the flat portion 150. To complete the package, the cover sheet 200 is sealed to the tray, and a vacuum is drawn within the sealed package.

The package of the present invention provides all of the advantages noted above. In particular, the reduction of waste material is accomplished by not including secondary means of support. Further, the package has a high degree of longitudinal stability provided primarily by the stabilizing edges, to avoid bending during shipment and handling. Moreover, withdrawal of the catheter from the package without undue stress to the preformed curves or bends of the distal tip of the catheter is facilitated.

The package of the present invention is also advantageous for other products which have similar requirements to the catheters described above; for example other types of catheters, or other flexible products which should not be bent during shipment or straightened upon withdrawal from the package.

The foregoing has been a description of several embodiments of the present invention, but is not intended to limit the invention in any way. Rather, many modifications, variations and changes in details may be made within the scope of the present invention.

What is claimed is:

1. The combination of a package and a medical catheter, wherein said package comprises:

an elongated tray having side walls and a bottom and having a first end and a second end, said tray including a relatively flat portion located near said first end of said tray, a hub retaining portion located near said second end of said tray, and a pair of ridges extending along a portion of the length of said tray between said hub retaining portion and said flat portion;

a cover sheet sealed to said tray; and means for providing longitudinal stability to said package;

wherein said catheter comprises:

a distal end;

a hub end; and an elongated main body extended between said distal end and said hub end;

wherein said distal end of said catheter is located on said flat portion of said tray, said hub end of said catheter is located within said hub retaining portion of said tray, and said elongated main body of said catheter is located between said pair of ridges of said tray; and wherein said cover sheet is sealed to said tray to form said package and said package has a vacuum applied thereto and wherein said means for providing longitudinal stability are formed when said vacuum is applied.

* * * * *